United States Patent
Robinson, Jr. et al.

(10) Patent No.: US 6,303,636 B1
(45) Date of Patent: Oct. 16, 2001

(54) ARYLSULFONYLAMINO HYDROXAMIC ACID DERIVATIVES

(75) Inventors: Ralph Pelton Robinson, Jr., Gales Ferry; Kim Francis McClure, Mystic, both of CT (US)

(73) Assignee: Pfizer Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/355,163

(22) PCT Filed: Jan. 12, 1998

(86) PCT No.: PCT/IB98/00023

§ 371 Date: Jul. 22, 1999

§ 102(e) Date: Jul. 22, 1999

(87) PCT Pub. No.: WO98/33768

PCT Pub. Date: Aug. 6, 1998

Related U.S. Application Data
(60) Provisional application No. 60/036,857, filed on Feb. 3, 1997.

(51) Int. Cl.[7] ............ A61K 31/445; A61K 31/395; C07D 211/66; C07D 205/04

(52) U.S. Cl. ............ 514/330; 514/210; 546/225; 548/953

(58) Field of Search ............ 546/225; 548/953; 514/330, 210

(56) References Cited

U.S. PATENT DOCUMENTS 5,804,593 * 9/1998 Warpehoski et al. ............ 514/419

FOREIGN PATENT DOCUMENTS

| | | | |
|---|---|---|---|
| 606046A1 | 7/1994 | (EP) | C07D/213/42 |
| 930067 | * 7/1999 | (EP) | . |
| 952148 | * 10/1999 | (EP) | . |
| 9600214 | 1/1996 | (WO) | C07D/213/42 |
| 9627583 | 9/1996 | (WO) | C07C/311/29 |
| 99/24399 | * 5/1999 | (WO) | . |
| 99/52889 | * 10/1999 | (WO) | . |

* cited by examiner

*Primary Examiner*—Ceila Chang
(74) *Attorney, Agent, or Firm*—Peter C. Richardson; Paul H. Ginsburg; Garth Butterfield

(57) ABSTRACT

A compound of the formula

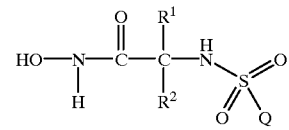

I wherein $R^1$, $R^2$ and Q are as defined above, useful in the treatment of a condition selected from the group consisting of arthritis, cancer, tissue ulceration, macular degeneration, restenosis, periodontal disease, epidermolysis bullosa, scleritis, and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (NSAID'S) and analgesics, and in combination with cytotoxic drugs such as adriamycin, daunomycin, cis-platinum, etoposide, taxol, taxotere and other alkaloids, such as vincristine, in the treatment of cancer,

8 Claims, No Drawings

ARYLSULFONYLAMINO HYDROXAMIC ACID DERIVATIVES

This is a 371 application of International Application PCT/IB98/00023 filed Jan. 12, 1998 which claimed priority to co-pending U.S. Provisional Application No. 60/036,857 filed Feb. 3, 1997.

The present invention relates to arylsulfonylamino hydroxamic acid derivatives which are inhibitors of matrix metalloproteinases or the production of tumor necrosis factor (TNF) and as such are useful in the treatment of a condition selected from the group consisting of arthritis, cancer, tissue ulceration, restenosis, periodontal disease, epidermolysis bullosa, scieritis and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (hereinafter NSAID'S) and analgesics for the treatment of arthritis, and in combination with cytotoxic drugs such as adriamycin, daunomycin, cis-platinum, etoposide, taxol, taxotere and alkaloids, such as vincristine, in the treatment of cancer.

This invention also relates to a method of using such compounds in the treatment of the above diseases in mammals, especially humans, and to pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. comeal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Fiers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62 S11).

The present invention relates to a compound of the formula

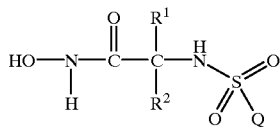

I or the pharmaceutically acceptable salts thereof, wherein $R^1$ and $R^2$ are each independently selected from $(C_1-C_6)$ alkyl, trifluoromethyl, trifluoromethyl$(C_1-C_6)$alkyl, $(C_1-C_6)$alkyl(difluoromethylene), $(C_1-C_3)$alkyl (difluoromethylene$(C_1-C_3)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl or $R^1$ and $R^2$ may be taken together to form a $(C_3-C_6)$cycloalkyl or benzofused $(C_3-C_6)$cycloalkyl ring or a group of the formula

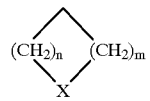

wherein n and m are independently 1 or 2 and X is $CF_2$, S, O or $NR^3$ wherein $R^3$ is hydrogen, $(C_1-C_6)$alkyl, $(C_6-C_{10})$ aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_1-C_6)$alkylsulfonyl, $(C_6-C_{10})$arylsulfonyl or acyl; and Q is $(C_1-C_6)$alkyl, $(C_6-C_{10})$aryl, $(C_6-C_{10})$aryloxy $(C_6-C_{10})$aryl, $(C_5-C_{10})$aryl$(C_6-C_{10})$aryl, $(C_6-C_{10})$aryl $(C_6-C_{10})$aryl$(C_1-C_6)$alkyl, $(C_6-C_{10})$aryl$(C_2-C_9)$ heteroaryl, $(C_6-C_{10})$aryloxy$(C_2-C_9)$heteroaryl, $(C_2-C_9)$heteroaryl, $(C_2-C_9)$heteroaryl$(C_2-C_9)$ heteroaryl, $(C_2-C_9)$heteroaryl$(C_6-C_{10})$aryl, $(C_1-C_6)$ alkyl$(C_6-C_{10})$aryl, $(C_1-C_6)$alkoxy$(C_6-C_{10})$aryl, $(C_1-C_{10})$aryl$(C_1-C_6)$alkoxy$(C_6-C_{10})$aryl, $(C_6-C_{10})$ aryl$(C_1-C_6)$alkoxy$(C_1-C_6)$alkyl, $(C_2-C_9)$ heteroaryloxy$(C_6-C_{10})$aryl, $(C_1-C_6)$alkyl$(C_2-C_9)$ heteroaryl, $(C_1-C_6)$alkoxy$(C_2-C_9)$heteroaryl, $(C_6-C_{10})$ aryl$(C_1-C_6)$alkoxy$(C_2-C_9)$heteroaryl, $(C_2-C_9)$ heteroaryloxy$(C_2-C_9)$heteroaryl, $(C_6-C_{10})$aryloxy $(C_1-C_6)$alkyl, $(C_2-C_9)$heteroaryloxy$(C_1-C_6)$alkyl, $(C_1-C_6)$alkyl$(C_6-C_{10})$aryloxy$(C_6-C_{10})$aryl, $(C_1-C_6)$ alkyl$(C_2-C_9)$heteroaryloxy$(C_6-C_{10})$aryl, $(C_1-C_6)$alkyl $(C_6-C_{10})$aryloxy$(C_2-C_9)$heteroaryl, $(C_1-C_6)$alkoxy $(C_6-C_{10})$aryloxy$(C_6-C_{10})$aryl, $(C_1-C_6)$alkoxy$(C_2-C_9)$ heteroaryloxy$(C_6-C_{10})$aryl or $(C_1-C_6)$alkoxy$(C_6-C_{10})$ aryloxy$(C_2-C_9)$heteroaryl wherein each aryl group is optionally substituted by fluoro, chloro, bromo, $(C_1-C_6)$alkyl, $(C_1-C_6)$alkoxy or perfluoro$(C_1-C_3)$ alkyl.

The term "alkyl", as used herein, unless otherwise indicated, includes saturated monovalent hydrocarbon radicals having straight, branched or cyclic moieties or combinations thereof.

The term "alkoxy", as used herein, includes 0-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes O-acyl groups wherein "acyl" is defined above.

The compound of formula I may have chiral centers and therefore exist in different enantiomeric forms. This invention relates to all optical isomers and stereoisomers of the compounds of formula I and mixtures thereof.

Preferred compounds of formula I include those wherein $R^1$ and $R^2$ are taken together to form a $(C_3-C_6)$cycloalkyl or benzo-fused $(C_3-C_6)$cycloalkyl ring or a group of the formula

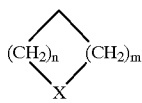

wherein n and m are independently 1 or 2 and X is $CF_2$, S, O or $NR^3$ wherein $R^3$ is hydrogen, $(C_1-C_6)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_1-C_6)$alkylsulfonyl, $(C_6-C_{10})$arylsulfonyl or acyl.

Other preferred compounds of formula I include those wherein $R^1$ and $R^2$ are taken together to form a $(C_3-C_6)$ cycloalkyl or benzo-fused $(C_3-C_6)$cycloalkyl ring.

Other preferred compounds of formula I include those wherein Q is $(C_6-C_{10})$aryl, $(C_6-C_{10})$aryl$(C_6-C_{10})$aryl, $(C_6-C_{10})$aryloxy$(C_6-C_{10})$aryl, $(C_6-C_{10})$aryloxy$(C_2-C_9)$heteroaryl, $(C_2-C_9)$heteroaryl, $(C_2-C_9)$heteroaryl$(C_2-C_9)$heteroaryl, $(C_6-C_{10})$aryl$(C_2-C_9)$heteroaryl $(C_2-C_9)$heteroaryl$(C_5-C_{10})$aryl or $(C_2-C_9)$heteroaryloxy$(C_6-C_{10})$aryl.

Other preferred compounds of formula I include those wherein Q is $(C_6-C_{10})$aryloxy$(C_6-C_{10})$aryl.

Other preferred compounds of formula I include those wherein $R^1$ and $R^2$ are each independently $(C_1-C_6)$alkyl.

More preferred compounds of formula I include those wherein $R^1$ and $R^2$ are taken together to form a $(C_3-C_6)$ cycloalkyl or benzo-fused $(C_3-C_6)$cycloalkyl ring or a group of the formula

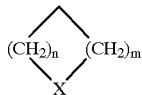

wherein n and m are independently 1 or 2 and X is $CF_2$, S, O or $NR^3$ wherein $R^3$ is hydrogen, $(C_1-C_6)$alkyl, $(C_6-C_{10})$ aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_1-C_6)$alkylsulfonyl, $(C_6-C_{10})$arylsulfonyl or acyl; and Q is $(C_6-C_{10})$aryl, $(C_6-C_{10})$aryl$(C_6-C_{10})$aryloxy$(C_6-C_{10})$aryloxy$(C_6-C_{10})$ aryl, $(C_6-C_{10})$aryloxy-$(C_2-C_9)$heteroaryl, $(C_2-C_9)$ heteroaryl, $(C_2-C_9)$heteroaryl$(C_2-C_9)$heteroaryl, $(C_6-C_{10})$ aryl$(C_2-C_9)$heteroaryl, $(C_2-C_9)$heteroaryl$(C_6-C_{10})$aryl or $(C_{29})$heteroaryloxy$(C_6-C_{10})$aryl.

More preferred compounds of formula I include those wherein $R^1$ and $R^2$ are taken together to form a $(C_3-C_6)$ cycloalkyl or benzo-fused $(C_3-C_6)$cycloalkyl ring; and Q is $(C_6-C_{10})$aryl, $(C_6-C_{10})$aryl$(C_6-C_{10})$aryl, $(C_6-C_{10})$aryloxy $(C_6-C_{10})$aryl, $(C_6-C_{10})$aryloxy$(C_2-C_9)$heteroaryl, $(C_2-C_9)$ heteroaryl, $(C_2-C_9)$heteroaryl$(C_2-C_9)$heteroaryl, $(C_6-C_{10})$ aryl$(C_2-C_9)$heteroaryl, $(C_2-C_9)$heteroaryl$(C_6-C_{10})$aryl or $(C_2-C_9)$heteroaryloxy$(C_6-C_{10})$aryl.

More preferred compounds of formula I include those wherein $R^1$ and $R^2$ are each independently $(C_1-C_6)$alkyl; and Q is $(C_6-C_{10})$aryl, $(C_6-C_{10})$aryl$(C_6-C_{10})$aryl, $(C_6-C_{10})$ aryloxy$(C_6-C_{10})$aryl, $(C_6-C_{10})$aryloxy$(C_2-C_9)$heteroaryl, $(C_2-C_9)$heteroaryl, $(C_2-C_9)$heteroaryl$(C_2-C_9)$heteroaryl, $(C_6-C_{10})$aryl$(C_2-C_9)$heteroaryl, $(C_2-C_9)$heteroaryl$(C_6-C_{10})$ aryl or $(C_2-C_9)$heteroaryloxy$(C_6-C_{10})$aryl.

More preferred compounds of formula I include those wherein $R^1$ and $R^2$ are each independently $(C_1-C_6)$alkyl; and Q is $(C_6-C_{10})$aryloxy$(C_6-C_{10})$aryl.

Specific preferred compounds of formula I include the following:

3-[4-(4-Fluorophenoxy)benzenesulfonylamino]azetidine-3-carboxylic acid hydroxyamide;

4-[4-(4-Fluorophenoxy)benzenesulfonylamino] piperidine-4-carboxylic acid hydroxyamide;

1-[4-(4-Fluorophenoxy)benzenesulfonylamino] cyclopropane-1-carboxylic acid hydroxyamide;

1-[4-(4-Chlorophenoxy)benzenesulfonylamino] cyclopropane-1-carboxylic acid hydroxyamide;

1-[4-(4-Fluorophenoxy)benzenesulfonylamino] cyclobutane-1-carboxylic acid hydroxyamide;

1-[4-(4-Chlorophenoxy)benzenesulfonylamino] cyclobutane-1-carboxylic acid hydroxyamide;

1-[4-(4-Fluorophenoxy)benzenesulfonylamino] cyclopentane-1-carboxylic acid hydroxyamide;

1-[4(4-Fluorophenoxy)benzenesulfonylamino] cyclohexane-1-carboxylic acid hydroxyamide;

2-[4-(4-Fluorophenoxy)benzenesulfonylamino]-N-hydroxy-2-methylpropionamide;

2-[4-(4-Chlorophenoxy)benzenesulfonylamino]-N-hydroxy-2-methyl-propionamide;

N-Hydroxy-2-methyl-2-(5pyridin-2-ylthiophene-2-sulfonylamino)propionamide;

1-(5-Pyridin-2-yl-thiophene-2-sulfonylamino) cyclopentane-1-carboxylic acid hydroxyamide;

1-(4'-Fluorobiphenyl-4-sulfonylamino)cyclopropane-1-carboxylic acid hydroxyamide;

1-(4'-Fluorobiphenyl-4-sulfonylamino)cyclobutane-1-carboxylic acid hydroxyamide;

1-(4'-Fluorobiphenyl-4-sulfonylamino)cyclopentane-1-carboxylic acid hydroxyamide;

2-(4-Methoxybenzenesufonylamino)indan-2-carboxylic acid hydroxyamide; and

2-[4-(4-Fluorophenoxy)benzenesulfonylamino]-indan-2-carboxylic acid hydroxyamide.

The present invention also relates to a pharmaceutical composition for (a) the treatment of a condition selected from the group consisting of arthritis, cancer, synergy with cytotoxic anticancer agents, tissue ulceration, macular degeneration, restenosis, periodontal disease, epidermolysis bullosa, scleritis, in combination with standard NSAID'S and analgesics and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of formula I or a pharmaceutically acceptable salt thereof effective in such treatments and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of formula I or a pharmaceutically acceptable salt thereof.

The present invention also relates to a method for treating a condition selected from the group consisting of arthritis, cancer, tissue ulceration, macular degeneration, restenosis, periodontal disease, epidermolysis bullosa, scieritis, compounds of formula I may be used in combination with standard NSAID'S and analgesics and in combination with cytotoxic anticancer agents, and other diseases characterized by matrix metalloproteinase activity, AIDS, sepsis, septic shock and other diseases involving the production of tumor necrosis factor (TNF) in a mammal, including a human, comprising administering to said mammal an amount of a compound of formula I or a pharmaceutically acceptable salt thereof effective in treating such a condition.

The following reaction Schemes illustrate the preparation of the compounds of the present invention. Unless otherwise indicated $R^1$, $R^2$ and Q in the reaction Schemes and the discussion that follow are defined as above.

mixture is stirred at a temperature between about 0° C. to about 500° C., preferably at room temperature, for a time period between about 10 minutes to about 2 days, preferably about 60 minutes.

In Reaction 3 of Preparation A, the intermediate compound of formula VI is hydrogenolyzed to provide the

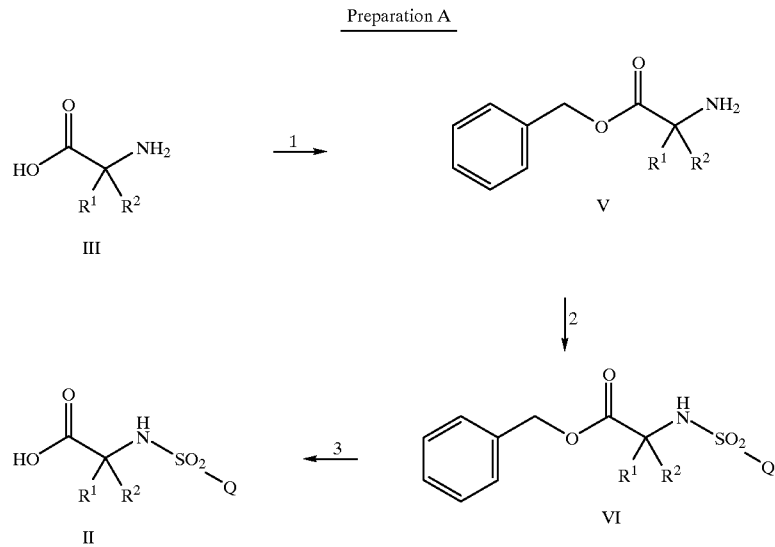

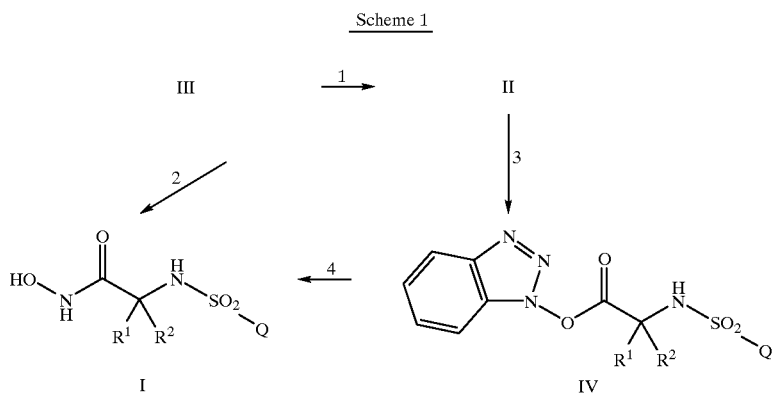

In Reaction 1 of Preparation A, an amino acid of formula III is treated with benzyl alcohol and an acid of the formula HX, wherein X is preferably 4-toluenesulfonate, in an inert solvent, such as benzene or toluene (toluene preferred) to obtain the corresponding benzyl ester acid salt of formula V. The reaction is normally carried out for a time period between about 1 hour to about 24 hours, at the boiling temperature of the solvent used. The water formed during the progress of the reaction is normally collected in a Dean-Stark trap.

In Reaction 2 of Preparation A, the compound of formula V is converted to the corresponding compound of formula VI by reacting V with a reactive functional derivative of a sulfonic acid ($QSO_2OH$), such as the sulfonyl chloride ($QSO_2Cl$), in the presence of a base, such as sodium hydroxide or triethylamine, and a solvent, such as methylene chloride, tetrahydrofuran, dioxane, water or acetonitrile, preferably a mixture of dioxane and water. The reaction intermediate of formula II. The reaction is carried out at in a solvent, such as ethanol, under an atmosphere of hydrogen (preferably at 3 atmospheres pressure) using a catalyst such as 10% palladium on activated carbon. The reaction mixture is normally agitated at room temperature for a time period between about 30 minutes to about 24 hours, preferably about 1.5 hours.

In reaction 1 of Scheme 1, the amino acid compound of formula III is converted to the corresponding compound of formula II by reacting III with a reactive functional derivative of a sulfonic acid of the formula $QSO_2OH$, wherein Q is as defined above, such as the sulfonyl chloride ($QSO_2Cl$), in the presence of a base, such as sodium hydroxide or triethylamine, and a polar solvent such as tetrahydrofuran, dioxane, water or acetonitrile, preferably a mixture of dioxane and water. The reaction mixture is stirred at a temperature between about 0° C. to about 50° C., preferably at room temperature, for a time period between 10 minutes to about 2 days, preferably about 60 minutes.

In reaction 2 of Scheme 1, the carboxylic acid of formula 11 is converted to the hydroxamic acid compound of formula I by treating II with 1-(3dimethylaminopropyl)-3-ethylcarbodiimide and 1-hydroxybenztriazole in a polar solvent, such as N,N-dimethylformamide, followed by the addition of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as triethylamine. Alternatively, a protected derivative of hydroxylamine or its salt form, where the hydroxyl group is protected as a tert-butyl, benzyl, allyl or 2-trimethylsilylethyl ether, may be used in place of hydroxylamine or a hydroxylamine salt. Removal of the hydroxyl protecting group is carried out by hydrogenolysis for a benzyl protecting group (5% palladium on barium sulfate is the preferred catalyst) or treatment with a strong acid, such as trifluoroacetic acid, for a tert-butyl protecting group. The allyl protecting group may be removed by treatment with tributyitinhydride and acetic acid in the presence of catalytic bis(triphenylphosphine) palladium(II)chloride. The 2-trimethylsilylethyl ether may be removed by reaction with a strong acid such as trifluoroacetic acid or by reaction with a fluoride source such as boron trifluoride etherate. The reaction of II with hydroxylamine, a salt of hydroxylamine, a protected derivative of hydroxylamine or a salt of a protected derivative of hydroxylamine may also be carried out the presence of (benztriazol-1-yloxy)tris(dimethylamino)-phosphonium hexafluorophosphate and a base such as triethylamine in an inert solvent, such as methylene chloride. The reaction mixture is stirred at a temperature between about 0° C. to about 50° C., preferably room temperature, for a time period between about 1 hour to about 3 days, preferably about 1 day. The preferred procedure for converting compound 11 to compound I is to react II with O-benzylhydroxylamine hydrochloride in the presence of (benztriazol-1-yloxy)tris(dimethylamino) phosphonium hexafluorophosphate and triethylamine using methylene chloride as solvent. Subsequent removal of the O-benzyl protecting group to afford a compound of formula I is then carried out by hydrogenolysis under 3 atmospheres hydrogen at room temperature using 5% palladium on barium sulfate as catalyst. The preferred solvent is methanol. The reaction time may vary from about 1 hour to about 5 hours (3.5 hours preferred).

In certain instances it is preferred to obtain the compound of formula I by reaction of hydroxylamine, a salt of hydroxylamine, a protected derivative of hydroxylamine or a salt of a protected derivative of hydroxylamine with an activated ester of formula IV, as shown in Reaction 3 of Scheme 1. The reaction is carried out in an inert solvent, such as N,N-dimethyl-formamide at a temperature ranging from about room temperature to about 80° C., preferably about 50° C. for a time period of about 1 hour to about 2 days. If a protected derivative of hydroxylamine or a salt of a protected derivative of hydroxylamine is used, removal of the protecting group is carried out as described above. The activated ester derivative of formula IV is obtained by treatment of the compound of formula 11 with (benztriazol-1-yloxy)tris(dimethylamino)-phosphonium hexafluorophosphate and a base such as triethylamine in an inert solvent, such as methylene chloride (Reaction 4, Scheme 1). The reaction mixture is stirred at a temperature between about 0° C. to about 50° C., preferably room temperature, for a time period between about 1 hour to about 3 days, preferably about 1 day.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium slats.

Similarly acid addition salts, such as of mineral acids, organic carboxylic and organic sulfonic acids e.g. hydrochloric acid, methanesutfonic acid, maleic acid, are also possible provided a basic group, such as pyridyl, constitutes part of the structure.

The ability of the compounds of formula I or their pharmaceutically acceptable salts (hereinafter also referred to as the compounds of the present invention) to inhibit matrix metalloproteinases or the production of tumor necrosis factor (TNF) and, consequently, demonstrate their effectiveness for treating diseases characterized by matrix metalloproteinase or the production of tumor necrosis factor is shown by the following in vitro assay tests.

Biological Assay

Inhibition of Human Collagenase (MMP-1)

Human recombinant collagenase is activated with trypsin using the following ratio: 10 $\mu$g trypsin per 100 $\mu$g of collagenase. The trypsin and collagenase are incubated at room temperature for 10 minutes then a five fold excess (50 $\mu$l/10 $\mu$g trypsin) of soybean trypsin inhibitor is added.

10 mM stock solutions of inhibitors are made up in dimethyl sulfoxide and then diluted using the following Scheme:

10 mM→120 $\mu$M→12 $\mu$M→1.2 $\mu$M→0.12 $\mu$M

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 $\mu$l is then added to appropriate wells of the microfluor plate. Final concentration of collagenase in the assay is 100 ng/ml.

Substrate (DNP-Pro-Cha-Gly-Cys(Me)-His-Ala-Lys (NMA)-NH$_2$) is made as a 5 mM stock in dimethyl sulfoxide and then diluted to 20 $\mu$M in assay buffer. The assay is initiated by the addition of 50 $\mu$l substrate per well of the microfluor plate to give a final concentration of 10 $\mu$M.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine IC$_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). IC$_{50}$'s are determined from the concentration of inhibitor that gives a signal that is 50% of the control.

If IC$_{50}$'s are reported to be <0.03 $\mu$M then the inhibitors are assayed at concentrations of 0.3 $\mu$M, 0.03 $\mu$M, 0.03 $\mu$M and 0.003 $\mu$M.

Inhibition of Gelatinase (MMP-2)

Inhibition of gelatinase activity is assayed using the Dnp-Pro-Cha-Gly-Cys(Me)-His-Ala-Lys(NMA)-NH$_2$ substrate (10 $\mu$M) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 µM, 3 µM, 0.3 µM and 0.03 µM. Each concentration is done in triplicate.

Fluorescence readings (360 nm excitation, 460 emission) are taken at time zero and then at 20 minutes intervals for 4 hours.

$IC_{50}$'s are determined as per inhibition of human collagenase (MMP-1). If $IC_{50}$'s are reported to be less than 0.03 µM, then the inhibitors are assayed at final concentrations of 0.3 µM, 0.03 µM, 0.003 µM and 0.003 µM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[CH$_2$CH(CH$_3$)$_2$]CO-Leu-Gly-OC$_2$H$_5$] yields a mercaptan fragment that can be monitored in the presence of Ellman's reagent.

Human recombinant prostromelysin is activated with trypsin using a ratio of 1 µl of a 10 mg/ml trypsin stock per 26 µg of stromelysin. The trypsin and stromelysin are incubated at 37° C. for 15 minutes followed by 10 µl of 10 mg/ml soybean trypsin inhibitor for 10 minutes at 37° C. for 10 minutes at 37° C. to quench trypsin activity.

Assays are conducted in a total volume of 250 µl of assay buffer (200 mM sodium chloride, 50 mM MES, and 10 mM calcium chloride, pH 6.0) in 96-well microliter plates. Activated stromelysin is diluted in assay buffer to 25 µg/ml. Eliman's reagent (3Carboxy-4-nitrophenyl disulfide) is made as a 1M stock in dimethyl formamide and diluted to 5 mM in assay buffer with 50 µl per well yielding at 1 mM final concentration.

10 mM stock solutions of inhibitors are made in dimethyl sulfoxide and diluted serially in assay buffer such that addition of 50 µL to the appropriate wells yields final concentrations of 3 µM, 0.3 µM, 0.003 µM, and 0.0003 µM. All conditions are completed in triplicate.

A 300 mM dimethyl sulfoxide stock solution of the peptide substrate is diluted to 15 mM in assay buffer and the assay is initiated by addition of 50 µl to each well to give a final concentration of 3 mM substrate. Blanks consist of the peptide substrate and Eliman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5mM calcium chloride, 20 µM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 µM, 3 µM, 0.3 µM, and 0.03 µM.

Substrate (Dnp-Pro-Cha-Gly-Cys(Me)-His-Ala-Lys (NMA)-NH$_2$) is prepared as for inhibition of human collagenase (MMP-1) and 50 µl is added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 µM, inhibitors are then assayed at final concentrations of 0.3 µM, 0.03 µM, 0.003 µM and 0.0003 µM.

Inhibition of TNF Production

The ability of the compounds or the pharmaceutically acceptable salts thereof to inhibit the production of TNF and, consequently, demonstrate their effectiveness for treating diseases invomng the production of TNF is shown by the following in vitro assay:

Human mononuclear cells were isolated from anticoagulated human blood using a one-step Ficoll-hypaque separation technique. (2) The mononuclear cells were washed three times in Hanks balanced salt solution (HBSS) with divalent cations and resuspended to a density of $2 \times 10^6$ /ml in HBSS containing 1% BSA. Differential counts determined using the Abbott Cell Dyn 3500 analyzer indicated that monocytes ranged from 17 to 24% of the total cells in these preparations.

180µ of the cell suspension was aliquoted into flate bottom 96 well plates (Costar). Additions of compounds and LPS (100 ng/ml final concentration) gave a final volume of 200 µl. All conditions were performed in triplicate. After a four hour incubation at 37° C. in an humidified $CO_2$ incubator, plates were removed and centrifuged (10 minutes at approximately 250×g) and the supernatants removed and assayed for TNFα using the R&D EUSA Kit.

For administration to mammals, including humans, for the inhibition of matrix metalloproteinases or the production of tumor necrosis factor (TNF), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), aJginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The present invention is illustrated by the following examples, but it is not limited to the details thereof.

PREPARATION A 4-(4-Fluorophenoxy)benzenesulfonyl chloride

Chlorosulfonic acid (26 mL, 0.392 mole) was added dropwise to ice-cooled 4-fluorophenoxybenzene (36.9 grams, 0.196 mole) with mechanical stirring. When addition was complete, the mixture was stirred at room temperature for 4 hours. The mixture was then poured into ice water. The product, 4-(4fluorophenoxy)benzene-sulfonylchloride (18.6 grams, 33%) was collected by filtration and dried in the air.

PREPARATION B

Sodium (3-methylbutoxy)benzenesulfonate

A solution of 4hydroxybenzenesulfonic acid (10.0 grams, 43.1 mmole) and sodium hydroxide (3.3 grams, 83 mmole) in water (40 mL) was mixed with a solution of 1-iodo-3methylbutane (11.3 mL, 86.4 mmole) in isopropanol (60 mL) and the resulting mixture was heated at reflux for 2 days. The isopropanol was removed by evaporation under vaccuum. The titled compound, 10.0 grams (87%), was collected by filtration washing with isopropanol.

PREPARATION C 4-(3-Methylbutoxy)benzenesulfonyl chloride

A mixture of sodium 4(3-methylbutoxy)benzenesulfonate (2.5 grams, 9.4 mmole), thionyl chloride (10 mL), and 5 drops of N,N-dimethylformamide was heated at reflux for 5 hours. After cooling, the excess thionyl chloride was evaporated and the residue was taken up in ethyl acetate. The solution was cooled in an ice bath and water was added. The organic phase was separated and washed with water and brine. After drying over sodium sulfate, the solvent was evaporated to afford the titled compound as an oil, 2.34 grams (95%).

PREPARATION D

Sodium 4-(2-cyclopentylethoxy)benzenesulfonate

A solution of 4-hydroxybenzenesulfonic acid (6.5 grams, 28.2 mmole) and sodium hydroxide (2.2 grams, 55 mmole) in water (15 mL) was mixed with a solution of 2-(bromoethyl)cyclopentane (15.0 grams, 84.7 mmole) in isopropanol (40 mL) and the resulting mixture was heated at reflux for 2 days. The isopropanol was removed by evaporation under vaccuum. The titled compound, 4.7 grams (57%), was collected by filtration washing with isopropanol.

PREPARATION E 4-(3-Methylbutoxy)benzenesulfonyl chloride

A mixture of sodium 4(2-cyclopentylethoxy)-benzenesulfonate (2.5 grams, 8.6 mmole), thionyl chloride (15 mL), and a few drops of N,N-dimethylformamide was heated at reflux for 5 hours. After cooling, the excess thionyl chloride was evaporated and the residue was taken up in ethyl acetate. The solution was cooled in an ice bath and water was added. The organic phase was separated and washed with water and brine. After drying over sodium sulfate, the solvent was evaporated to afford the titled compound as an oil, 2.24 grams (90%).

PREPARATION F

4'-Fluorobiphenylsuffonyl chloride

Chlorosuifonic acid (8.7 mL, 0.13 mole) was added dropwise to 4fluorobiphenyl (10.2 grams, 59 mmol) while sirring in an ice bath. Stirring was continued with ice cooling for 0.5 hours and then the reaction mixture was poured onto ice. The resulting white precipitate was collected by filtration and dissolved in chloroform. The chloroform solution was washed with water and brine, dried over magnesium sulfate and concentrated to afford a white solid. The desired product, 4'-fluorobiphenylsulfonyl chloride (4.3 grams, 27%), was separated from 4'-fluorobiphenylsulfonic acid (an unwanted side product) by crystallization of the latter from ethyl acetate and crystallization of the remaining material from hexane.

PREPARATION G

Sodium 4-(4-fluorobenzyloxy)benzenesulfonate

To a solution of 4-hydroxybenzenesulfonic acid (5.13 grams, 22.1 mmole) in 1 N aqueous sodium hydroxide solution (23 mL) was added a solution of 4-fluorobenzylbromide (3.3 mL, 26.5 mmole) in ethanol (20 mL). The resulting mixture was heated at reflux for 2 days. Upon cooling and standing, a white solid precipitated. The precipitated product, sodium 4-(4-fluorobenzyloxy) benzenesulfonate, 4.95 grams (74%) was collected by filtration washing with ethyl acetate and diethyl ether.

PREPARATION H

4(4-Fluorobenzyloxy)benzenesulfonyl chloride

To a slurry of sodium 4(4-fluorobenzyloxy) benzenesulfonate (0.5 grams, 1.64 mmole), in methylene chloride (5 mL) was added phosphorus pentachloride (275 mg, 1.31 mmole). The resulting mixture was heated at reflux for 7 hours. After cooling in an ice bath and quenching with water (15 mL), the mixture was extracted with ethyl acetate. The organic phase was washed brine, dried over sodium sulfate, and concentrated to afford 4-(4-fluorobenzyloxy) benzenesulfonyl chloride a white solid (130 mg, 26%).

PREPARATION I

4(4-Chlorophenoxy)benzenesulfonyl chloride

Chlorosulfonic acid (9.7 mL, 0.147 mole) was added dropwise to 4-chlorophenoxybenzene (12.6 mL, 73.4 mmole) at room temperature with stirring. When addition was complete, the mixture was stirred at room temperature for 1 hour and then poured into ice water. The solid was collected by filtration, dried in the air, and recrystallized from petroleum ether and ethyl acetate to give 4-(4-chlorophenoxy)benzenesulfonylohloride (7.43 grams, 33%).

EXAMPLE 1
1-(4-Methoxybenzenesulfonylamino)cyclopentane-1-carboxyllcacidhydroxyamide (A) To a solution of 1-aminocyclopentane-1-carboxylic acid (6.0 grams, 46.5 mmole) and triethylamine (14 mL, 100 mmole) in dioxane (90 mL) and water (90 mL) was added 4methoxybenzenesulfonyl chloride (10.6 grams, 51.3 mmole). The resulting mixture was stirred at room temperature for 4 hours, acidified with aqueous 1N hydrochloric acid solution, and extracted twice with ethyl acetate. The combined ethyl acetate extracts were washed with brine, dried over magnesium sulfate and concentrated to leave a tan solid which was triturated with chloroform to afford 1-(4-methoxybenzenesulfonylamino)-cyclopentane-1 carboxylic acid as a white solid, 5.42 grams (39%).

(B) To a solution of 1-(4-methoxybenzenesulfonylamino)cyclopentane-1-carboxylic acid (4.65 grams, 15.2 mmole) and triethylamine (2.5 mL, 17.9 mmole) in methylene chloride (120 mL) was added (benzotriazol-1-yloxy)tris(dimethylamino)phosphonium hexafluorophosphate (7.4 grams, 16.3 mmole). The resulting mixture was stirred at room temperature for 2.5 days. The solvent was evaporated and the residue was taken up in ethyl acetate. The solution was washed successively with aqueous 0.5 N hydrochloric acid solution, water and brine. After drying over magnesium sulfate, the solvent was evaporated to afford 1-(4-methoxybenzenesulfonylamino)cyclopentane carboxylic acid benzotriazol-i -yl ester as a yellow solid. This was dissolved in N,N-dimethylformamide (120 mL) and to the resulting solution was added diisopropylethylamine (5.3 mL, 30 mmole) and 0-benzylhydroxylamine hydrochloride (3.2 grams, 20 mmole). The mixture was heated in an oil bath at 50° C. for 20 hours. The solvent was evaporated and ethyl acetate was added. The mixture was filtered to collect a white solid. The filtrate was washed successively with aqueous 0.5 N hydrochloric acid solution, aqueous saturated sodium bicarbonate solution and brine. Upon evaporation of the solvent, a solid was obtained which was combined with that isolated by filtration and triturated with ethyl acetate to afford 1-(4-methoxybenzenesulfonylamino)cyclopentane-1-carboxylic acid benzyloxyamide as a white solid, 2.92 grams (47%).

(C) A solution of 1-(4methoxybenzenesulfonylamino)cyclopentane-1-carboxylic acid benzyloxyamide (1.50 grams, 3.71 mmole) in methanol (200 mL) was treated with 5% palladium on barium sulfate (0.75 grams) and hydrogenated at 3 atmospheres pressure for 3.5 hours in a Parr shaker. The catalyst was removed by passage through a 0.45 μm nylon filter and the filtrate was concentrated to afford 1-(4-methoxybenzenesulfonylamino)-cyclopentane-1-carboxylic acid hydroxyamide as a white solid, 1.13 grams (97%). MS: 313 (M−1).

The titled compounds of Examples 28 were prepared by a method analogous to that described in Example 1 using the reagents indicated.

EXAMPLE 2
1-(4-Methoxybenzenesulfonylamino)cyclohexane-1-carboxylic acid hydroxyamide 1-Aminocyclohexane-1-carboxylic acid; 4-methoxybenzenesulfonyl chloride. MS: 327 (M−1).

EXAMPLE 3
1-[4-(4-Fluorophenoxy)benzenesulfonylamino]cyclodentane-1-carboxylic acid hydroxyamide 1-Aminocyclopentane-1-carboxylic acid; 4-(4-fluorophenoxy)benzenesulfonyl chloride. MS: 393 (M−1). Analysis calculated for $C_{16}H_{19}FN_2O_5S.0.25\ H_2O$: $C_{54.19}$, H 4.93, N 7.02. Found: $C54.20$, H 5.13, N 7.08.

EXAMPLE 4
1-[4-(4-Fluorophenoxy)benzenesulfonylamino]cyclohexane-1-carboxylic acid hydroxyamide 1-Aminocyclohexane-1-carboxylic acid; 4-(4-fluorophenoxy)benzenesulfonyl chloride. Recrystallized from chloroform. MP: 174° C.; MS: 407 (M−1).

EXAMPLE 5
1-[4-(4-Fluorophenoxy)benzenesulfonylamino]cyclopropane-1-carboxylic acid hydroxyamide 1-Aminocyclopropane-1-carboxylic acid; 4-(4-fluorophenoxy)benzenesuffonyl chloride. MP: 184° C.; MS 365 (M−1); Analysis calculated for $C_{16}H_{15}FN_2O_5S$: $C_{52.45}$, H 4.13, N 7.65. Found: $C_{52.20}$, H 4.34, N 7.44.

EXAMPLE 6
1-(4'-Fluorobiphenyl-4-sulfonylamino)cyclopentane-1-carboxylic acid hydroxyamide 1-Aminocyclopentane-1-carboxylic acid; 4'-fluorobiphenylsulfonyl chloride. Recrystallized from chloroform. MP 159° C.; MS: 377 (M−1).

EXAMPLE 7
1-[4-(4-Fluorophenoxy)benzenesulfonylamino]cyclobutane-1-carboxylic acid hydroxyamide 1-Aminocyclobutane-1-carboxylic acid; 4-(fluorophenoxy)benzenesulfonyl chloride. MS: 379 (M−1).

EXAMPLE 8
1-[4-(4-Fluorobenzyloxy)benzenesulfonylamino]cyclopropanecarboxylic acid hydroxyamide 1-Aminocyclopropane-1-carboxylic acid; 4-(4-fluorobenzyloxy)benzenesulfonyl chloride. MS: 379 (M−1).

EXAMPLE 9
N-Hydroxy-2-(4-methoxybenzenesulfonylamino)-2-methylproplonamide (A) A solution of 2-amino-2-methylpropionic acid benzyl ester hydrochloride (12.0 grams, 52.2 mmole) and 4-methoxybenzenesulfonylchloride (11.9 grams, 57.6 mmole) in dioxane (100 mL) and water (100 mL) was cooled in an ice bath. Triethylamine (18.2 mL, 0.13 mole) was then added. The ice bath was removed and the reaction mixture was allowed to stir at room temperature for 2 days. The solvents were removed under vacuum and the residue was taken up in ethyl acetate and water. The aqueous layer was separated and extracted twice with ethyl acetate. The combined organic layers were washed with aqueous saturated sodium bicarbonate solution, aqueous 1 N hydrochloric acid solution, and brine. After drying over sodium sulfate, the solvent was evaporated to leave a yellow oil (19.3 grams) a portion of which (10 grams) was chromatographed on silica gel eluting with 3:7 ethyl acetate/hexane to afford, after recrystallization from ethyl acetate/hexane, 2-(4-methoxybenzenesulfonylamino)-2-methylpropionic acid benzyl ester as a white solid, 6.59 grams (67%).

(B) A solution of 2-(4-methoxybenzenesulfonyamino)-2-methylpropionic acid benzyl ester (1.5 grams, 4.13 mmole) in ethanol (80 mL) was treated with 10% palladium on carbon (0.17 grams) and hydrogenated at 3 atmospheres pressure for 1.5 hours in a Parr shaker. The catalyst was removed by passage through a 0.45 μm nylon filter and the filtrate was concentrated to afford 2-(4methoxybenzenesulfonylamino)-2-methylpropionic acid as a white solid, 1.09 grams (96%).

(C) A solution of 2-(4methoxybenzenesulfonylamino)-2-methylpropionic acid (1.08 grams, 3.95 mmole) in methylene chloride (120 mL) was cooled in an ice bath. Triethylamine (2.2 mL, 15.8 mmole), (benzotriazol-1-yloxy)tris(dimethylamino)-phosphonium hexafluorophosphate (2.6 grams, 5.88 mmole) and O-benzylhydroxylamine hydrochloride (0.95 grams, 5.95 mmole) were subsequently added. The resulting mixture was stirred at room temperature for 16 hours. The solvent was evaporated and the residue was taken up in ethyl acetate. The solution was washed successively with aqueous 1 N hydrochloric acid solution, aqueous saturated sodium bicarbonate solution, water and brine. After drying over sodium sulfate, the solvent was evaporated to afford an oil from which the desired product, N-benzyloxy-2-(4-methoxybenzenesulfonylamino)-2-methyl-propionamide (1.41 grams, 95%), a white solid, was obtained by chromatography on silica gel eluting with 1:2 ethyl acetate/hexanes.

(D) A solution of N-benzyloxy-2-(4-methoxybenzenesulfonylamino)-2-methyl-propionamide (1.40 grams, 3.70 mmole) in methanol (80 mL) was treated with 5% palladium on barium sulfate (0.75 grams) and hydrogenated at 3 atmospheres pressure for 1.5 hours in a Parr shaker. The catalyst was removed by passage through a 0.45 µm nylon filter and the filtrate was concentrated to afford N-hydroxy-2-(4-methoxy-benzenesulfonylamino)-2-methylpropionamide as a white solid, 1.06 grams (100%). MP: 122–125° C. MS: 289 (M+1): Analysis calculated for $C_{11}H_{16}N_2O_5S$: C, 45.82; H, 5.59; N, 9.72; Found: C, 45.88; H, 5.60; N, 9.69.

The titled compounds of Examples 10–12 were prepared by a method analogous to that described in Example 9 using the reagents indicated.

EXAMPLE 10

2-[4-(4-Fluorophenoxy)benzenesulfonylamino]-N-hydroxy-2-methyl-proplonamide

2-Amino-2-methylpropionic acid benzyl esterhydrochloride; (4-fluorophenoxy)-benzenesulfonyl chloride. MP: 133–134° C. MS: 369 (M+1), Analysis calculated for $C_{16}H_{17}FN_2O_5S$: C, 52.17; H, 4.65; N, 7.60; Found: C, 52.21; H, 4.83; N, 7.80.

EXAMPLE 11

N-Hydroxy-2-methyl-2-[4-(3-methylbutoxy)benzenesulfonylamino]-proplonamide

2-Amino-2-methylpropionic acid benzyl ester hydrochloride; 4-(3-methylbutoxy)-benzenesulfonyl chloride. Recrystallized from ethyl acetate/hexane. MP 126.5–128° C. MS: 343 (M–1), Analysis calculated for $C_{15}H_{24}N_2O_5S$: C, 52.31; H, 7.02; N, 8.13; Found: C, 52.30; H, 7.07; N, 8.16.

EXAMPLE 12

2-[4-(2-cyclopentylethoxy)benzenesulfonylamino]-N-hydroxy-2-methyl-proplonamide

2-Amino-2-methylpropionic acid benzyl ester hydrochloride; 4-(2-cyclopentylethoxy) benzenesulfonyl chloride. Recrystallized from ethyl acetate/hexane. MP 126–127° C. MS: 369 (M–1). Analysis calculated for $C_{17}H_{26}N_2O_5S$: $C_{55.12}$, H 7.07, N 7.56. Found: $C_{55.46}$, H 7.09, N 7.38.

EXAMPLE 13

N-Hydroxy-2-methyl-2-(5pyridin-2-ylthlophene-2-sulfonylamino)propionamide (A) To a solution of 2-amino-2-methylpropionic acid (2.0 grams, 19.4 mmole) in 1 N aqueous sodium hydroxide solution (45 mL) and dioxane (45 mL) was added 5-pyridin-2-ylthiophene-2-sulfonyl chloride (8.41 grams, 32.4 mmole). The resulting mixture was stirred at room temperature for 16 hours. Additional 1 N aqueous sodium hydroxide solution (45 mL) was added to the reaction mixture which was then extracted with diethyl ether. The organic extracts were discarded. The aqueous layer was acidified with 1 N hydrochloric acid solution and extracted with ethyl acetate. The ethyl acetate fractions were washed with brine, dried over magnesium sulfate and concentrated to afford 2-methyl-2-(5pyridin-2-ylthiophene-2-sulfonylamino) propionic acid as a white solid (2.18 grams, 34%).

(B) To a solution of 2-methyl-2-(5-pyridin-2-ylthiophene-2-sulfonylamino)-propionic acid (1.60 grams, 4.91 mmole) in methylene chloride (160 mL) was added triethylamine (2.3 mL, 16.5 mmole), (benzotriazol-1-yloxy)tris(dimethylamino)-phosphonium hexafluorophosphate (2.4 grams, 5.41 mmole) and O-(2-trimethylsilylethyl) hydroxylamine hydrochloride (0.92 grams, 5.41 mmole). The resulting mixture was stirred at room temperature for 16 hours. The solvent was evaporated and the residue was taken up in ethyl acetate. The solution was washed with water, aqueous saturated sodium bicarbonate solution, and brine. After drying over magnesium sulfate, the solvent was evaporated to afford a white foam from which the desired product, 2-methyl-2-(5-pyridin-2-ylthiophene-2-sulfonylamino)-N-(2-trimethylsilanylethoxy)-propionamide (220 mg, 10%), a white solid, was isolated by chromatography on silica gel eluting with 3:2 ethyl acetate/hexanes.

(C) 2-Methyl-2-(5-pyridin-2-ylthiophene2-sufonylamino)-N-(2-tdmethylsilanylethoxy)propionamide (80 mg, 0.18 mmole) was dissolved in trifluoroacetic acid and the resulting solution was stirred at room temperature for 16 hours. The trifluoroacetic acid was evaporated under vacuum, chasing with methanol, to afford N-hydroxy-2-methyl-2-(5-pyridin-2-ylthiophene2-sulfonylamino) propionamide, a yellow oil (60 mg, 97%) which was crystallized from ethanol. MP 165–166° C. MS: 342 (M+1).

The titled compounds of Examples 14–15 were prepared by a method analogous to that described in Example 13 using the reagent indicated.

EXAMPLE 14

1-(5-Pyridin-2-yl-thiophene-2-sulfonylamino) cyclopentane-1-carboxylic acid hydroxyamide 1-Aminocyclopentane-1-carboxylic acid; 5pyridin-2-ylthiophene-2-sulfonyl chloride. MS: 368 (M+1).

EXAMPLE 15

1-[4-(4-Chlorophenoxy)benzenesulfonylamino] cyclopropane-1-carboxylic acid hydroxyamide 1-Aminocyclopropane-1-carboxylic acid; 4-(4-chlorophenoxy)benzenesufonyl chloride. MS: 381 (M–1).

What is claimed is:

1. A compound of the formula

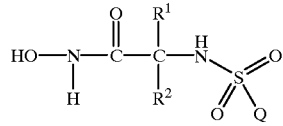

I or the pharmaceutically acceptable salts thereof, wherein $R^1$ and $R^2$ are taken together to form a group of the formula

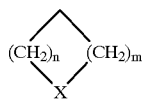

wherein n and m are independently 1 or 2 and X is O or $NR^3$ wherein $R^3$ is hydrogen, $(C_1-C_6)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_1-C_6)$alkylsulfonyl, $(C_6-C_{10})$arylsulfonyl or acyl; and Q is $(C_1-C_6)$alkyl, $(C_6-C_{10})$aryl, $(C_6-C_{10})$aryloxy$(C_6-C_{10})$aryl, $(C_6-C_{10})$aryl$(C_6-C_{10})$aryl, $(C_6-C_{10})$aryl$(C_6-C_{10})$aryl$(C_1-C_6)$alkyl, $(C_6-C_{10})$aryl$(C_2-C_9)$heteroaryl, $(C_6-C_{10})$aryloxy$(C_2-C_9)$heteroaryl, $(C_2-C_9)$heteroaryl, $(C_2-C_9)$heteroaryl$(C_2-C_9)$heteroaryl, $(C_2-C_9)$heteroaryl$(C_6-C_{10})$aryl, $(C_1-C_6)$alkyl$(C_6-C_{10})$aryl, $(C_1-C_6)$alkoxy$(C_6-C_{10})$aryl, $(C_6-C_{10})$aryl$(C_1-C_6)$alkoxy$(C_6-C_{10})$aryl, $(C_6-C_{10})$aryl$(C_1-C_6)$alkoxy$(C_1-C_6)$alkyl, $(C_2-C_9)$heteroaryloxy$(C_6-C_{10})$aryl, $(C_1-C_6)$alkyl$(C_2-C_9)$heteroaryl, $(C_1-C_6)$alkoxy$(C_2-C_9)$heteroaryl, $(C_6-C_{10})$aryl$(C_1-C_6)$alkoxy$(C_2-C_9)$heteroaryl, $(C_2-C_9)$heteroaryloxy$(C_2-C_9)$heteroaryl, $(C_6-C_{10})$aryloxy$(C_1-C_6)$alkyl, $(C_2-C_9)$heteroaryloxy$(C_1-C_6)$alkyl, $(C_1-C_6)$alkyl$(C_6-C_{10})$aryloxy$(C_6-C_{10})$aryl, $(C_1-C_6)$alkyl$(C_2-C_9)$heteroaryloxy$(C_6-C_{10})$aryl, $(C_1-C_6)$alkyl$(C_6-C_{10})$aryloxy$(C_2-C_9)$heteroaryl, $(C_1-C_6)$alkoxy$(C_6-C_{10})$aryloxy$(C_6-C_{10})$aryl, $(C_1-C_6)$alkoxy$(C_2-C_9)$heteroaryloxy$(C_6-C_{10})$aryl
or $(C_1-C_6)$alkoxy$(C_6-C_{10})$aryloxy$(C_2-C_9)$heteroaryl wherein each aryl group is optionally substituted by fluoro, chloro, bromo, $(C_1-C_6)$alkyl $(C_1-C_6)$alkoxy
or perfluoro$(C_1-C_3)$alkyl.

2. A compound according to claim 1, wherein $R^1$ and $R^2$ are taken together to form a group of the formula

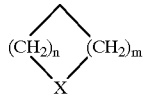

wherein n and m are independently 1 or 2 and X is O or $NR^3$ wherein $R^3$ is hydrogen, $(C_1-C_6)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_1-C_6)$alkylsulfonyl, $(C_6-C_{10})$arylsulfonyl or acyl.

3. A compound according to claim 1, wherein Q is $(C_6-C_{10})$aryl, $(C_6-C_{10})$aryl $(C_6-C_{10})$aryl, $(C_6-C_{10})$aryloxy $(C_6-C_{10})$aryl, $(C_6-C_{10})$aryloxy$(C_2-C_9)$heteroaryl, $(C_2-C_9)$heteroaryl, $(C_2-C_9)$heteroaryl$(C_2-C_9)$heteroaryl, $(C_6-C_{10})$aryl$(C_2-C_9)$heteroaryl, $(C_2-C_9)$heteroaryl$(C_6-C_{10})$aryl or $(C_2-C_9)$heteroaryloxy$(C_6-C_{10})$aryl.

4. A compound according to claim 4, wherein Q is $(C_6-C_{10})$aryloxy$(C_6-C_{10})$aryl.

5. A compound according to claim 1, wherein $R^1$ and $R^2$ are taken together to form a group of the formula

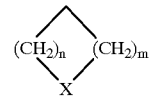

wherein n and m are independently 1 or 2 and X is $NR^3$ wherein $R^3$ is hydrogen, $(C_1-C_6)$alkyl, $(C_6-C_{10})$aryl, $(C_2-C_9)$heteroaryl, $(C_6-C_{10})$aryl$(C_1-C_8)$alkyl, $(C_2-C_9)$heteroaryl$(C_1-C_6)$alkyl, $(C_1-C_6)$alkylsulfonyl, $(C_6-C_{10})$arylsulfonyl or acyl; and Q is $(C_6-C_{10})$aryl, $(C_6-C_{10})$aryl$(C_6-C_{10})$aryl, $(C_6-C_{10})$aryloxy$(C_6-C_{10})$aryl, $(C_6-C_{10})$aryloxy-$(C_2-C_9)$heteroaryl, $(C_2-C_9)$heteroaryl, $(C_2-C_9)$heteroaryl$(C_2-C_9)$heteroaryl, $(C_6-C_{10})$aryl$(C_2-C_9)$heteroaryl, $(C_2-C_9)$heteroaryl$(C_1-C_{10})$aryl or $(C_2-C_9)$heteroaryloxy$(C_6-C_{10})$aryl.

6. A compound according to claim 1, wherein said compound is selected from the group consisting of:

3-[4-(4-Fluorophenoxy)benzenesulfonylamino]azetidine-3-carboxylic acid hydroxyamide; and 4-[4-(4-Fluorophenoxy)benzenesulfonylamino] piperidine-4-carboxylic acid hydroxyamide.

7. A pharmaceutical composition for the treatment of a condition selected from the group consisting of arthritis, cancer, tissue ulceration, muscular degeneration, restenosis, periodontal disease, epidermolysis bullosa, scleritis, in combination with standard NSAID'S and analgesics and in combination with cytotoxic anticancer agents, sepsis, septic shock in a mammal, comprising an amount of a compound of claim 1 effective in said treatment and a pharmaceutically acceptable carrier.

8. A method for treating a condition selected from the group consisting of arthritis, cancer, tissue ulceration, muscular degeneration, restenosis, periodontal disease, epidermolysis bullosa, scleritis, compounds of formula I may be used in combination with standard NSAID'S and analgesics and in combination with cytotoxic anticancer agents, sepsis, septic shock in a mammal, comprising administering to said mammal an amount of a compound of claim 1, effective in treating a said condition.

* * * * *